United States Patent [19]

Goldenberg et al.

[11] Patent Number: 4,470,974
[45] Date of Patent: Sep. 11, 1984

[54] GASTRIC CYTOPROTECTION WITH L-363,586

[75] Inventors: Marvin M. Goldenberg, Westfield; Doris L. Keller, Edison, both of N.J.

[73] Assignee: Merck & Co., Inc., Rahway, N.J.

[21] Appl. No.: 507,850

[22] Filed: Jun. 27, 1983

[51] Int. Cl.³ ............................................. A61K 37/00
[52] U.S. Cl. ................................................... 424/177
[58] Field of Search .................. 260/112.5 S; 424/177

[56] References Cited

U.S. PATENT DOCUMENTS 4,310,518  1/1982  Freidinger et al. .......... 260/112.5 S
4,370,348  1/1983  Shriver ................................. 424/331

OTHER PUBLICATIONS

Chem. Abstr. vol. 98, (1983) 84216j.
Biol. Abstr. 65, (1978) 64207.
Chem. Abstr. vol. 98, (1983) 752v.
Chem. Abstr. vol. 94, (1981) 76964d.
Chem. Abstr. vol. 91, (1979) 117810j.
Chem. Abstr. vol. 87, (1977) 63200g.
Chem. Abstr. vol. 89, (1978) 53800e.
S. Szabo et al., Experimentia 38, 254 (1982) "Cytoprotection-Organoprotection by Somatostatin . . . ".
S. Szabo et al., Science 214, 200 (1981) "Sulfhydryl Compounds May Mediate Gastric Cytoprotection".

*Primary Examiner*—Delbert R. Phillips
*Attorney, Agent, or Firm*—Gabriel Lopez; Ernest V. Linek; Hesna J. Pfeiffer

[57] ABSTRACT

The somatostatin analog L-363,586 is a cyclic hexapeptide having the structure; cyclo-(N-methyl-Ala-Tyr-d-Trp-Lys-Val-Phe). L-363,586 has been found to be useful for inducing gastric cytoprotection via a mechanism not involving the inhibition of gastric acid secretions. Specific therapeutic utilities include, erosive gastritis, erosive esophagitis, inflammatory bowel disease and ethanol induced hemorrhagic gastric erosions.

8 Claims, 2 Drawing Figures

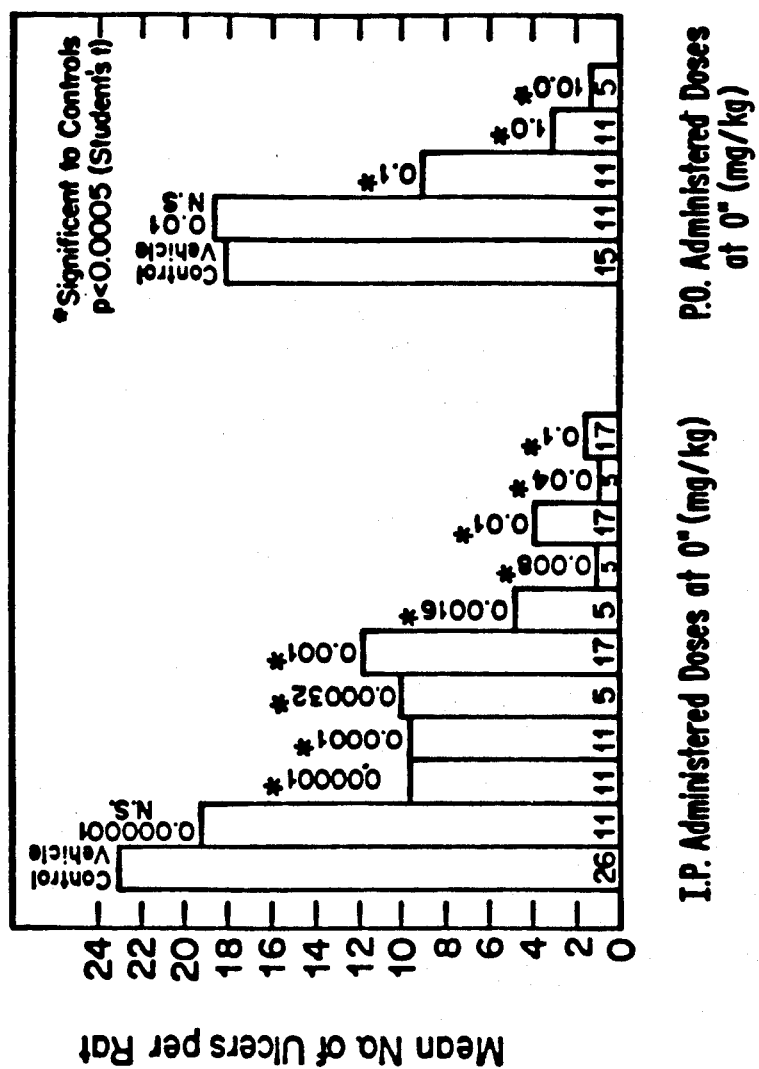

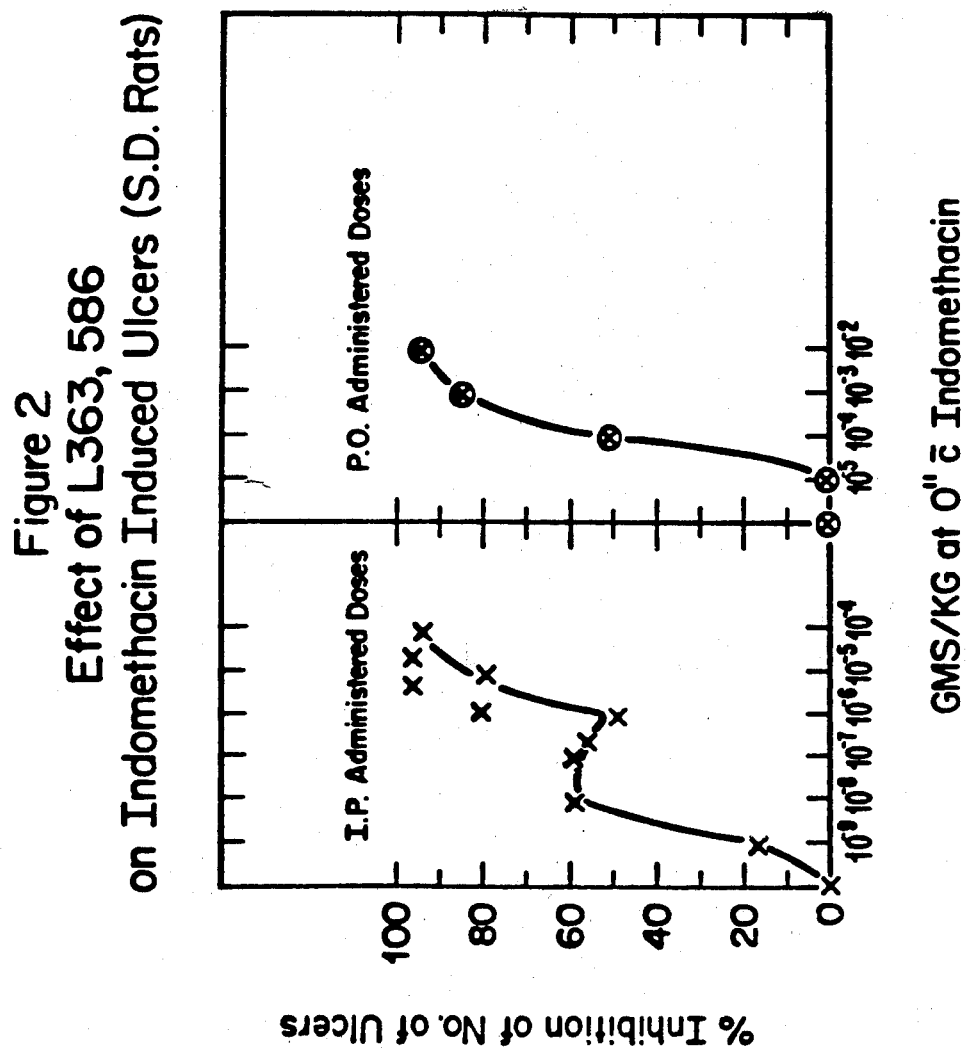

GASTRIC CYTOPROTECTION WITH L-363,586

BACKGROUND OF THE INVENTION

L-363,586 is a somatostatin analog described in Freidinger et al., U.S. Pat. No. 4,310,518 which is herein incorporated by reference.

L-363,586 has the structure; cyclo-(N-methyl-Ala-Tyr-d-Trp-Lys-Val-Phe) wherein the abbreviated amino acid components are defined as follows; Ala-, 1-alanine; Tyr-, 1-tyrosine; d-Trp-, d-Tryptophan; Lys-, 1-lysine; Val-, 1-valine; and Phe-, 1-phenylalanine.

L-363,586 is reported in U.S. Pat. No. 4,310,518 to be useful for inhibiting the release of glucagon, growth hormone and insulin. The compound is also described therein as being useful for inhibiting the release of gastric acid secretions.

Gastic cytoprotection not involving the inhibition of gastric acid secretions, is a known phenomenon. For example, prostaglandin F2$\beta$ does not inhibit gastric acid secretion, but the compound does induce gastric cytoprotection. Other prostaglandins induce gastric cytoprotection at much smaller dose levels than those required for the inhibition of gastric acid secretion. See for example, Shriver, U.S. Pat. No. 4,370,348.

Somatostatin has been reported to produce gastric cytoprotection. However, this effect is reported to be dependent on the presence of endogenous sulfhydryl groups. Somatostatin analogs lacking such endogenous sulfhydryl groups do not induce cytoprotection. See: S. Szabo et al., Experimentia 38 254 (1982).

It has been discovered that L-363,586, a somatostatin analog devoid of endogenous sulfhydryl groups, is useful for inducing gastric cytoprotection via a mechanism not involving the inhibition of gastric acid secretions.

BRIEF DESCRIPTION OF THE DRAWINGS

FIG. 1 shows the marked reduction in the number of ulcers by L-363,586 in the indomethacin-induced ulcer assay described in Example B.

FIG. 2 shows the percent inhibition of ulcer formation by L-363,586 in the indomethacin-induced ulcer assay described in Example B.

SUMMARY OF THE INVENTION

L-363,586 and its non-toxic acid addition salts have been found useful for inducing gastric cytoprotection.

DETAILED DESCRIPTION

This invention is directed to the use of L-363,586 as a cytoprotective agent. Cytoprotection mechanisms are not well defined. However, it is clear that lower dosages of cytoprotective agents are required for effectiveness than are required to inhibit gastric acid secretions. Because of its cytoprotective nature, L-363,586 may be used to treat or prevent disease states such as, erosive gastritis, erosive esophagitis, inflammatory bowel disease and ethanol-induced hemorrhagic erosions.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays were used to measure the cytoprotective ability of L-363,586. These assays were; (A) an ethanol-induced lesion assay and (B) an indomethacin-induced ulcer assay.

L-363,586 was found to inhibit hemorrhagic lesions by up to 68% in the ethanol-induced lesion assay (See Example A) when single doses up to 4.4 mg/kg were administered perorally (p.o.) simultaneously with 100% ethanol. A dose as low as 0.44 mg/kg of L-363,586 was significantly effective in protecting against ethanol-induced lesions.

L-363,586 was found to exhibit a dose-dependent reduction in gastric mucosal ulcers when administered either p.o. or i.p. in the indomethacin-induced ulcer assay (See Example B). When L-363,586 was administered simultaneously with indomethacin (See FIG. 1), significant ulcer reduction was observed at 10 nanograms per kilogram (i.p.) and when administered p.o., significant ulcer reduction was observed at 0.1 mg/kg.

Based on the data obtained in these assays, the effective daily dosage level for L-363,586 for inducing cytoprotection in mammals, especially humans, will range from about 0.005 $\mu$g/kg to about 0.1 $\mu$g/kg, preferably from about 0.001 $\mu$g/kg to about 0.01 $\mu$g/kg.

Any suitable route of administration may be employed for providing a mammal, especially a human with the effective dosage of L-363,586. For example, oral, parenteral, intramuscular, intraveneous and the like may be employed. Dosage forms include tablets, troches, dispersions, suspensions, solutions, capsules and the like.

In practical use, L-363,586 can be combined as the active ingredient in intimate admixture with a pharmaceutical carrier according to conventional pharmaceutical compounding techniques. The carrier may take a wide variety of forms depending on the form of preparation desired for administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease of administration, tablets and capsules represent the most advantageous oral dosage unit form, in which case solid pharmaceutical carriers are obviously employed. If desired, tablets may be sugar coated or enteric coated by standard techniques.

In addition to L-363,586, the pharmaceutical composition may also contain other active ingredients, such as non-steroidal anti-inflammatory agents e.g., indomethacin, ibuprofen, sulindac, fenbufen, and the like, or peripheral analgesic agents such as zomepirac, diflunisal and the like.

EXAMPLES

A. Ethanol-Induced Lesion Assay

Twenty-four hr. fasted Sprague-Dawley (S.D.) rats were perorally (p.o.) dosed with 1.0 ml absolute ethanol. Fifteen min. prior to ethanol administration, groups of rats each received either an aqueous vehicle (aqueous methylcellulose 5% wt.) or L-363,586, at doses ranging from 0.037 to 3.0 mg/kg perorally. One hour later, the animals were sacrificed and stomach mucosae were examined for resulting lesions. No prophylactic effect by L-363,586 was observed.

When the aqueous vehicle was given p.o. simultaneously with 100% ethanol, the effective dilution of alcohol did not diminish the number of resulting lesions. In contrast, Table 1 shows that when L-363,586 was given simultaneously p.o. with 100% ethanol, it significantly reduced the lesion score in a dose dependent manner, i.e., 4.4 mg/kg inhibited lesions by 60% while lower doses were less effective.

TABLE 1
Effect of L-363,586 P.O. Dosed O" with Ethanol (A) in the Ethanol-Induced Lesion Assay

| No. Rats | Compound | mg/kg | Gastric Lesions Mean Score + SEM | % Inhibition | P Value |
|---|---|---|---|---|---|
| 26 | Aqueous Vehicle | — | 2.5 ± 0.1 (1) | 0 | — |
| 12 | L-363,586 | 0.22 | 2.3 ± 0.3 (1) | 8.0 | >0.05 |
| 12 | L-363,586 | 0.44 | 1.8 ± 0.4 (1) | 28.0 | <0.025 |
| 18 | L-363,586 | 1.0 | 1.8 ± 0.3 (1) | 28.0 | <0.025 |
| 12 | L-363,586 | 2.2 | 1.5 ± 0.4 (1) | 40.0 | <0.005 |
| 18 | L-363,586 | 4.4 | 1.0 ± 0.3 (1) | 60.0 | <0.0005 |

(A) Vehicle or compound in 0.5 ml volume is co-administered with 1.0 ml 100% ethanol.
(1) Pooled data from 3 assays; 60 minutes after ethanol.

B. Indomethacin-induced Ulcer Assay

Indomethacin, 20 mg/kg p.o., was used to induce ulcers in the 24 hr. fasted S.D. rat. Four experiments were performed to demonstrate the effect of L-363,586 when administered intraperitoneally (i.p.) immediately following indomethacin. Two experiments were performed to demonstrate the effect of L-363,586 when co-administered perorally with indomethacin. Table 2 describes the effect of L-363,586 when co-administered perorally (p.o.) with indomethacin.

TABLE 2
Gastric Cytoprotection By L-363,586 P.O.*

| No. Rats | Compound | Dose mg/kg | Number of Gastric Ulcers M + S.E.M. | % Inhibition of Gastric Ulcers |
|---|---|---|---|---|
| 15 | Indomethacin + Vehicle | 20 | 18.1 ± 1.6 | 0 |
| 11 | Indomethacin + L-363,586 | 20 0.01 | 18.6 ± 4.4 | −2.8 |
| 11 | Indomethacin + L-363,586 | 20 0.1 | 9.0 ± 1.9 | 50.3** |
| 11 | Indomethacin + L-363,586 | 20 1.0 | 3.0 ± 1.3 | 83.4** |

*Administered simultaneously with indomethacin
**Statistically significantly different from control; p = <0.05

The number of ulcers for twenty-six (i.p.) and fifteen (p.o.) aqueous vehicle-dosed control animals in the indomethacin ulcer assay were so close, (23.0±2.2 S.E.M. i.p.; 18.1±1.6 S.E.M. p.o.), that the data from each experimental dosage group were pooled for group statistical analysis by way of Student's "t" test. FIG. 1 indicates the number of ulcers resulting from indomethacin at 20 mg/kg p.o., when either 0.5% (wt.) aqueous methylcellulose vehicle or L-363,586 was co-administered. The bold-faced numbers at the bottom of each column represent the number of rats used for each value, while the dose, in mg/kg, is noted at the top of each column. L-363,586 administered i.p. at 0.00001 mg/kg (10 nanograms/kg), effectively reduced the number of ulcers by 58.3%, while increasing log-dose amounts to 0.001 mg/kg did not effectively reduce the damage any further. Higher i.p. doses, from 0.0016 to 0.1 mg/kg, thereafter, inhibited ulcer formation by 80% to 94%. FIG. 2 shows the percent inhibition of ulcer formation, describing doses in grams/kg.

FIGS. 1 and 2 also indicate the response to L-363,586 when administered perorally (p.o.).

The 0.1 mg/kg p.o. dose level inhibited ulcer formation by 50.3% while increasing this level to 0.5 or 1.0 mg/kg inhibited ulcer formation by 83% and 93%, respectively.

Native somatostatin, at doses up to 0.1 mg/kg i.p. was not effective in the peroral (p.o.) indomethacin-induced ulcer assay. Table 3 however, illustrates that when i.p. dose levels were increased to 0.5 or 1.0 mg/kg, the indomethacin-induced damage was then reduced by 62.4% and 46.3% respectively.

TABLE 3
Effect of I. P. Somatostatin on the Indomethacin-Induced Ulcer Assay

| Number Rats | Compound | mg/kg | Gastric Ulcers Mean Score + SEM* | % Inhibition | P Value |
|---|---|---|---|---|---|
| 20 | 0.5% methylcellulose | — | 20.5 ± 2.3 | 0 | — |
| 5 | somatostatin | 0.0001 | 22.4 ± 3.8 | −9.3 | 0.05 |
| 5 | " | 0.001 | 21.0 ± 2.4 | 2.4 | 0.05 |
| 5 | " | 0.01 | 17.2 ± 2.3 | 16.1 | 0.05 |
| 10 | " | 0.1 | 19.3 ± 3.3 | 5.9 | 0.05 |
| 6 | " | 0.5 | 7.7 ± 3.6 | 62.4 | 0.01 |
| 11 | " | 1.0 | 11.0 ± 3.0 | 46.3 | 0.0125 |

Vehicle or compound dosed 10 ml/kg i.p. immediately following 20 mg/kg p.o. indomethacin.
*Pooled data from 3 assays; number of ulcers observed 4 hours after indomethacin.

As indicated above, inducement of gastric cytoprotection by L-363,586 is unrelated to the inhibition of gastric acid secretion. Although the mechanism of gastric cytoprotection is unknown, it appears that cytoprotective compounds increase the resistance of gastric mucosal cells to the necrotizing effect of strong irritants. It is suggested, therefore, that L-363,586, by a mechanism other than inhibition of gastric acid secretion, maintains the cellular integrity of the gastric mucosa and will thus be beneficial in the treatment of those disease states wherein injury to the gastric mucosa is present.

Claims to the invention follow.

What is claimed is:

1. The method of inducing cytoprotection in mammals by increasing the natural integrity of the gastrointestinal mucosa which comprises administering to a mammal in need of such therapy a cytoprotective-effective amount of L-363,586 in a pharmaceutically acceptable carrier.

2. The method of claim 1 wherein L-363,586 is administered orally.

3. The method of claim 1 wherein L-363,586 is administered in daily unit dosage form.

4. The method of claim 1 wherein L-363,586 is administered at a dosage level of from 0.005 to 0.1 μg/kg.

5. The method of preventing gastrointestinal lesions in mammals which comprises administering to said mammal in need of such therapy a cytoprotective-effective amount of L-363,586 in a pharmaceutically acceptable carrier.

6. The method of claim 5 wherein L-363,586 is administered at a dosage level of from 0.001 to 0.01 μg/kg.

7. The method of treating gastrointestinal lesions in mammals which comprises administering to said mammal in need of such therapy a cytoprotective-effective amount of L-363,586 in a pharmaceutically acceptable carrier.

8. The method of claim 7 wherein L-363,586 is administered at a dosage level of from 0.005 to 0.1 μg/kg.

* * * * *